United States Patent
Stapelbroek et al.

(10) Patent No.: US 8,990,992 B2
(45) Date of Patent: Mar. 31, 2015

(54) MOUTHPIECE FOR CLEANING TEETH WITH A MECHANICAL DRIVE TRAIN

(71) Applicant: Koninklijke Philips N.V., Eindhoven (NL)

(72) Inventors: Martinus Bernardus Stapelbroek, Eindhoven (NL); Patrick A. Headstrom, Seattle, WA (US); Fokke Roelof Voorhorst, Eindhoven (NL); Jelte Steur, Eindhoven (NL); Arif Veendijk, Eindhoven (NL); Gert H. Westrup, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/312,752

(22) Filed: Jun. 24, 2014

(65) Prior Publication Data

US 2014/0298602 A1 Oct. 9, 2014

Related U.S. Application Data

(63) Continuation of application No. 13/704,077, filed as application No. PCT/IB2011/051792 on Apr. 25, 2011, now Pat. No. 8,793,830.

(60) Provisional application No. 61/357,260, filed on Jun. 22, 2010.

(51) Int. Cl.
| | |
|---|---|
| *A61C 17/22* | (2006.01) |
| *A61C 17/26* | (2006.01) |
| *A46B 9/04* | (2006.01) |
| *A46B 13/02* | (2006.01) |

(Continued)

(52) U.S. Cl.
CPC .............. *A61C 17/26* (2013.01); *A46B 9/045* (2013.01); *A46B 13/02* (2013.01); *A61C 17/228* (2013.01); *A61C 17/3481* (2013.01); *A61C 17/00* (2013.01)
USPC ................ 15/22.1; 15/22.2; 15/22.4; 433/41

(58) Field of Classification Search
USPC ............. 15/22.1, 22.2, 22.4; 433/41; 601/142
See application file for complete search history.

(56) References Cited

U.S. PATENT DOCUMENTS

| | | | |
|---|---|---|---|
| 4,011,616 A | * | 3/1977 | Kennedy ........................ 15/21.1 |
| 4,224,710 A | | 9/1980 | Solow |

(Continued)

FOREIGN PATENT DOCUMENTS

| | | |
|---|---|---|
| DE | 3337054 A1 | 10/1985 |
| JP | 8038256 A | 2/1996 |

(Continued)

*Primary Examiner* — Monica Carter
*Assistant Examiner* — Michael Jennings

(57) ABSTRACT

The mouthpiece appliance includes an assembly for receiving teeth (12) which includes a plurality of cleansing portions, typically two opposing side portions (14, 16) and an intermediate center portion (18). The brushing portions include bristle sections which are adapted to clean teeth. The appliance includes at least one DC motor assembly (26) with an output shaft with an eccentric mass of crankshaft (28). The appliance further includes a mechanical motor cover comprising a plurality of arm members which are arranged to connect the DC motor assembly to the cleansing portions of the appliance so that as the unbalanced weight on the output shaft rotates, movement of the cleansing portions, toward and away from the teeth or along the surfaces of the teeth occurs, producing cleansing of the teeth.

6 Claims, 11 Drawing Sheets

(51) Int. Cl.
 *A61C 17/34* (2006.01)
 *A61C 17/00* (2006.01)

(56) References Cited

U.S. PATENT DOCUMENTS

| | | | | |
|---|---|---|---|---|
| 5,177,827 A * | 1/1993 | Ellison | | 15/22.1 |
| 5,421,726 A * | 6/1995 | Okada | | 433/216 |
| 5,504,958 A * | 4/1996 | Herzog | | 15/22.1 |
| 6,353,956 B1 * | 3/2002 | Berge | | 15/22.1 |
| 6,526,982 B1 * | 3/2003 | Strong | | 128/848 |
| 7,082,638 B2 * | 8/2006 | Koh | | 15/22.1 |
| 7,409,741 B2 | 8/2008 | Dworzan | | |
| 7,757,693 B2 * | 7/2010 | Toussaint | | 128/848 |
| 8,122,890 B2 | 2/2012 | Vaska | | |
| 8,359,692 B2 | 1/2013 | Brewer | | |
| 2003/0162146 A1 | 8/2003 | Shortt et al. | | |
| 2004/0128777 A1 * | 7/2004 | Koh | | 15/22.1 |
| 2005/0196725 A1 | 9/2005 | Fu | | |
| 2005/0266370 A1 * | 12/2005 | Suzuki | | 433/29 |
| 2007/0292819 A1 | 12/2007 | Scarberry et al. | | |
| 2008/0003540 A1 | 1/2008 | Khawaled et al. | | |
| 2008/0233541 A1 | 9/2008 | De Vreese et al. | | |
| 2008/0257358 A1 | 10/2008 | Stern et al. | | |
| 2009/0061379 A1 | 3/2009 | Yamamoto et al. | | |
| 2009/0120446 A1 | 5/2009 | Vaska et al. | | |
| 2009/0120447 A1 | 5/2009 | Vaska et al. | | |
| 2009/0188058 A1 | 7/2009 | Schwarz-Hartmann et al. | | |
| 2010/0132720 A1 | 6/2010 | Razmovski | | |
| 2010/0242969 A1 | 9/2010 | Lyons | | |
| 2010/0288290 A1 * | 11/2010 | Lee et al. | | 128/861 |
| 2010/0311007 A1 | 12/2010 | Eliyahov | | |
| 2011/0180076 A1 | 7/2011 | Hegde et al. | | |

FOREIGN PATENT DOCUMENTS

| | | |
|---|---|---|
| WO | 0247512 A1 | 6/2002 |
| WO | 2004062518 A2 | 7/2004 |
| WO | 2006114291 A2 | 11/2006 |
| WO | 2007121760 A1 | 11/2007 |
| WO | 2008142600 A1 | 11/2008 |
| WO | 2009123965 A1 | 10/2009 |

* cited by examiner

MOUTHPIECE FOR CLEANING TEETH WITH A MECHANICAL DRIVE TRAIN

This application claims the benefit or priority of and describes relationships between the following applications: wherein this application is a continuation of U.S. patent application Ser. No. 13/704077, filed Dec. 13, 2012, which is the National Stage of International Application No. PCT/IB2011/051792, filed Apr. 25, 2011, which claims the priority of U.S. Provisional Patent Application Ser. No. 61/357,260, filed Jun. 22, 2010, all of which are incorporated herein in whole by reference.

This invention relates generally to mouthpieces for cleaning teeth and more specifically concerns a mouthpiece with a mechanical drive train arrangement which includes a motor with an eccentric mass as part of the drive train.

The possibility of teeth cleaning by a mouthpiece appliance involves special structural considerations. Axial movement of mouthpiece sections, with bristles thereon, moving toward and away from sections of teeth is one possible arrangement. Typically, the mouthpiece is driven by a motor and two or more connecting arm assemblies which produce desired motion of two or more associated mouthpiece sections. With axial motion, the length of the movement stroke of the mouthpiece sections is limited because of space limitations in the mouths of users. The movement of the mouthpiece sections is also complicated since the bristles in the mouthpiece will in operation impact different teeth from different directions because of the particular physical arrangement of the teeth relative to the particular configuration of the mouthpiece. In addition, effective teeth cleaning by a mouthpiece assembly is complicated by the fact that the mouthpiece is not a handheld device per se like a toothbrush so that the user's hand cannot be a reference point which the forces produced in operation by the mouthpiece bristles can react against.

In one arrangement the mouthpiece is divided into three separate sections, two side sections and a center section, all three of which are driven in such a manner that a significant component of their movement is toward and away from the teeth to produce the axial, i.e. tapping, cleaning action. The drive train for producing such an action should be reliable and produce the desired action in an efficient and effective manner.

Accordingly, one aspect of the article is a mouthpiece appliance for cleaning teeth, comprising: an assembly for receiving teeth which includes two opposing side portions and an intermediate center portion, wherein the side portions and the center portion include bristle sections which are adapted to clean teeth of the user when contact is made between the bristle sections and the surfaces of the teeth; a motor assembly with an output shaft and an eccentric mass or crankshaft mounted thereon; first and second opposing drive arms extending outwardly from and connected to the motor assembly so that the distal ends of the drive arms move outwardly and inwardly together; connecting arms connected to the drive arms and at one end to the side portions of the teeth receiving assembly so that as the motor shaft rotates, the side portions of the teeth receiving assembly move in and out, toward and away from the teeth, producing cleansing of the teeth; and a center member driven by the motor assembly, directly or by action of the two connecting arms, to move the center portion of the teeth receiving assembly toward and away from the teeth, producing cleansing of the teeth.

Another aspect of the article is a mouthpiece for cleaning teeth, comprising: an assembly for receiving teeth which includes two side portions and an intermediate center portion, wherein the side portions and the center portion include bristle sections which are adapted to clean teeth upon contact between the bristle sections and the teeth of the user; three motor assemblies, each with an eccentric weight mounted on an output shaft thereof; first, second and third drive arms which extend, respectively, between the respective motor assemblies and the side and center portions of the teeth receiving assembly; and first, second and third spring assemblies which connect the drive arms to a body portion of the appliance, wherein each of the spring assemblies, respectively, is configured to permit movement of their associated drive arm in one direction which results in cleansing of the teeth, but substantially prevents movement of the same drive arm in other directions.

A still further aspect of the article is a mouthpiece appliance for cleaning teeth, comprising: an assembly for receiving teeth which includes two opposing side portions and an intermediate center portion, wherein the side portions and the center portion include bristle sections which are adapted to clean the teeth of the user when contact is made between the bristle sections and surfaces of the teeth; a motor assembly, including an eccentric mass mounted on a drive shaft of the motor; an inner frame member which is connected to the motor assembly, the motor assembly and the inner frame member being supported so as to move toward and away from the teeth, but not in other dimensions; an outer frame member which includes an upper portion and a lower portion connected by separate hinge members, wherein the lower portion is fixed within the appliance and wherein the upper portion terminates in two free ends defining a distance therebetween; two connecting arms which extend between the inner frame and the upper portion of the outer frame, wherein rotation of the motor and the eccentric will produce an out and in movement of the upper portion of the outer frame member about the hinge members; two opposing side portion drive arms which extend respectively from the free ends of the upper portion of the outer frame member to the side sections of the teeth receiving assembly; and a center portion drive assembly extending between the inner frame member and the center portion of the teeth receiving assembly, such that of rotation of the motor and the eccentric results in an in and out movement of the side and center portions toward and away from the teeth, producing cleansing of the teeth by contact between the bristles and the teeth.

Another aspect of the article comprises: A mouthpiece appliance for cleaning teeth, comprising: an assembly for receiving teeth which includes two opposing side portions and an intermediate center portion, wherein the side portions and the center portion include bristle sections which are adapted to clean teeth of the user in operation; two connecting arms which cross one another and which are connected at one end to the opposing side portions of the teeth receiving assembly and are pivotally connected where they cross; a first linear motor connected between the other ends of the two connecting drive arms, wherein in operation the first linear motor drives the one ends of the drive arms toward and away from each other, resulting in the side portions moving toward and away from the teeth, producing cleansing of the teeth; a movable central member attached to the center section of the teeth receiving assembly and a fixed member positioned between the two drive arms a distance away from the central member; and a second linear motor extending between the fixed and movable members, wherein in operation the movable central member and the center section of the teeth receiving assembly move toward and away from the teeth, producing cleansing of the teeth.

Figure 1:
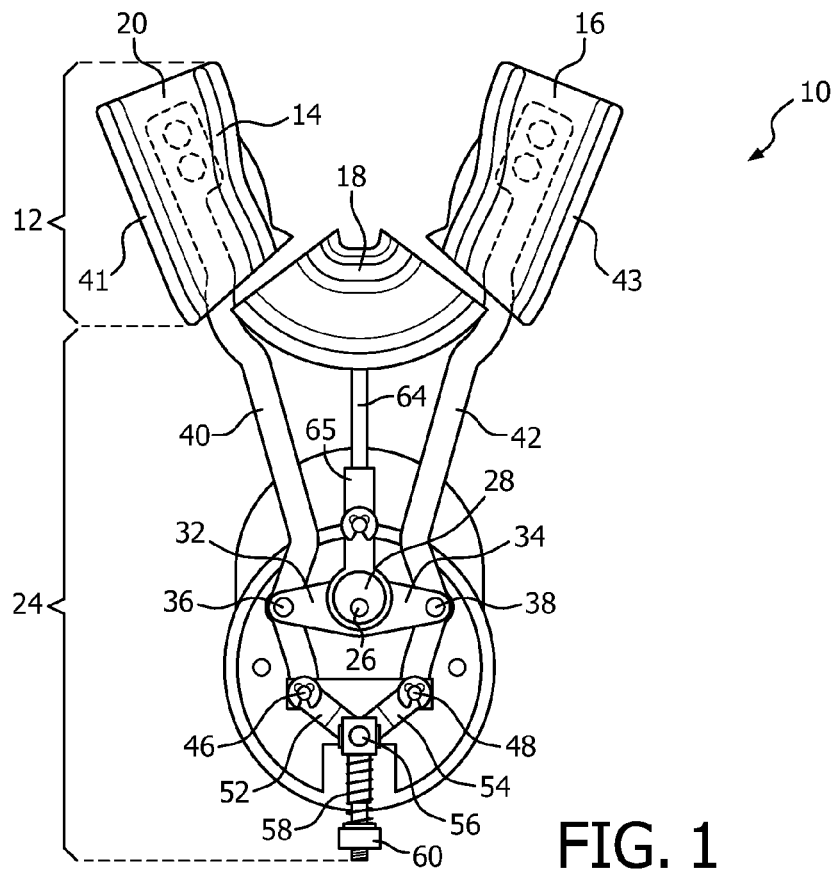
FIG. 1 is a top view of a first embodiment of a mouthpiece assembly.
Figure 2:
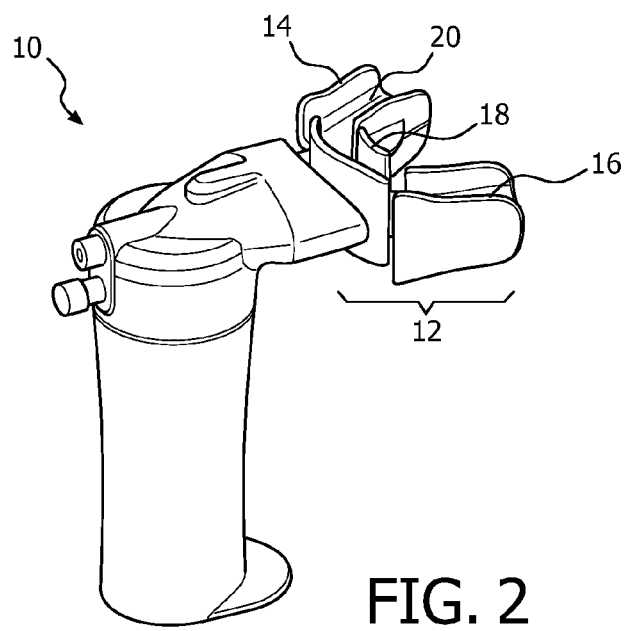
FIG. 2 is an isometric view of the mouthpiece assembly of FIG. 1.

FIGS. 1 and 2 show a first embodiment for a teeth cleaning mouthpiece with a mechanical drive train. The mouthpiece assembly 10 includes a teeth receiving assembly 12 which includes two generally opposing side portions 14, 16 and an intermediate center portion 18 positioned between the two side portions. The teeth receiving assembly 12 typically comprises a base of plastic material configured to receive the teeth of the user. The teeth receiving assembly could be adapted to include just the bottom teeth, or just the top teeth or both the top and bottom teeth. The individual side and center portions are formed so as to extend along the upper surfaces and the side surfaces of the teeth, covering the teeth surfaces.

Positioned on the interior surfaces of the side and center portions of the teeth receiving assembly are conventional bristles 20 which are adapted to produce a teeth cleaning action in operation of the mouthpiece. The bristles are similar to those used in conventional toothbrushes. However other elements could be used for teeth cleaning as well. It should be understood that the three portions of the teeth receiving assembly can take various arrangements and configurations. Typically, the teeth receiving assembly of the present invention will include three separate portions, although fewer than three portions could be used, such as just two portions, each covering up to one-half of the teeth surfaces, or in some cases just a center portion, covering a portion of the total number of teeth. More than three sections could also be used, with each section being driven independently or jointly with other sections, depending on the particular arrangement.

The three portions 14, 16 and 18 of the teeth receiving assembly 12 are driven mechanically. The center portion 18 is driven directly toward and away from the front teeth of the user. The two side portions are driven somewhat at an angle relative to the teeth in the side regions, i.e. those teeth to the rear of the front teeth, due to the particular mechanical arrangement of the drive train assembly, as discussed in detail below. There is, however, a significant component of the motion directed toward and away from the teeth.

A drive train assembly referred to generally at 24 includes a DC drive motor 26 and an eccentric mass 28 which is mounted on the output shaft of the motor. Alternatively, an eccentric crankshaft can be used. In the embodiment shown, the DC motor runs at a frequency of 10-100 Hz, preferably 25 Hz. The distance of the offset weight is 0.05-3 mm, preferably 0.1 to 0.5 mm. The characteristics of the motor and the eccentric, however, can be varied. The drive train assembly further includes two opposing drive arms 32 and 34 which extend directly outwardly from the motor 26 and are connected to the motor in such a manner that the distal ends 36 and 38 of the drive arms 32 and 34, respectively, move inwardly and outwardly together as the drive motor shaft and the eccentric rotate.

The length of the stroke or the distance that that the distal ends 36 and 38 move is approximately 0-1-2 mm, preferably 0.1 mm. Rotatably connected to distal ends 36 and 38 of the drive arms are opposing connecting arms 40 and 42 which extend toward the teeth receiving assembly and connect at free ends 41 and 43 thereof to side portions 14 and 16 of the teeth receiving assembly. In the embodiment of FIGS. 1 and 2, and further illustrated more functionally in FIG. 3, the connecting arms 40, 42 extend to the rear, away from the teeth, past distal ends 36 and 38 of drive arms 32, 34 to connecting points 46 and 48, about which the connecting arms rotate as the motor shaft and eccentric rotate. Extending from connecting points 46 and 48 and angled toward each other are two lower adjusting arms 52 and 54, connected at a center pivot point 56. Extending from pivot point 56 away from motor 26 is an adjusting arm 58 at the end of which is an adjustment knob 60. Rotation of adjustment knob 60 will move adjusting arm 58 toward or away from the motor, expanding or contracting the distance between the free ends 41, 43 of connecting arms 40 and 42, to accommodate wider positioned teeth in users' mouths. Although the adjustable feature of arms 52 and 54 with adjusting arm 58 is convenient, it is not necessary to the present invention.

In operation, the connecting arms 40, 42 will pivot about connecting points 46 and 48, as the two drive arms 32, 34 move in opposing directions, inwardly and outwardly by the action of motor 26. This results in a movement of the free ends 41, 43 of the connecting arms of 0.1-5 mm, preferably 0.5 mm, towards (against) and away from the respective side regions of the teeth. In the embodiment shown the connecting arms 40, 42 first angle slightly inwardly from their connection points with distal ends 36 and 38 of drive arms 32, 34. At this point, approximately 7.5 mm from the distal ends 36 and 38, the two connecting arms 40, 42 first angle outwardly at an angle which is approximately 5-15°, up to an approximately 40° inclusive angle, in the embodiment shown. This angle, however, can also vary.

Figure 3:
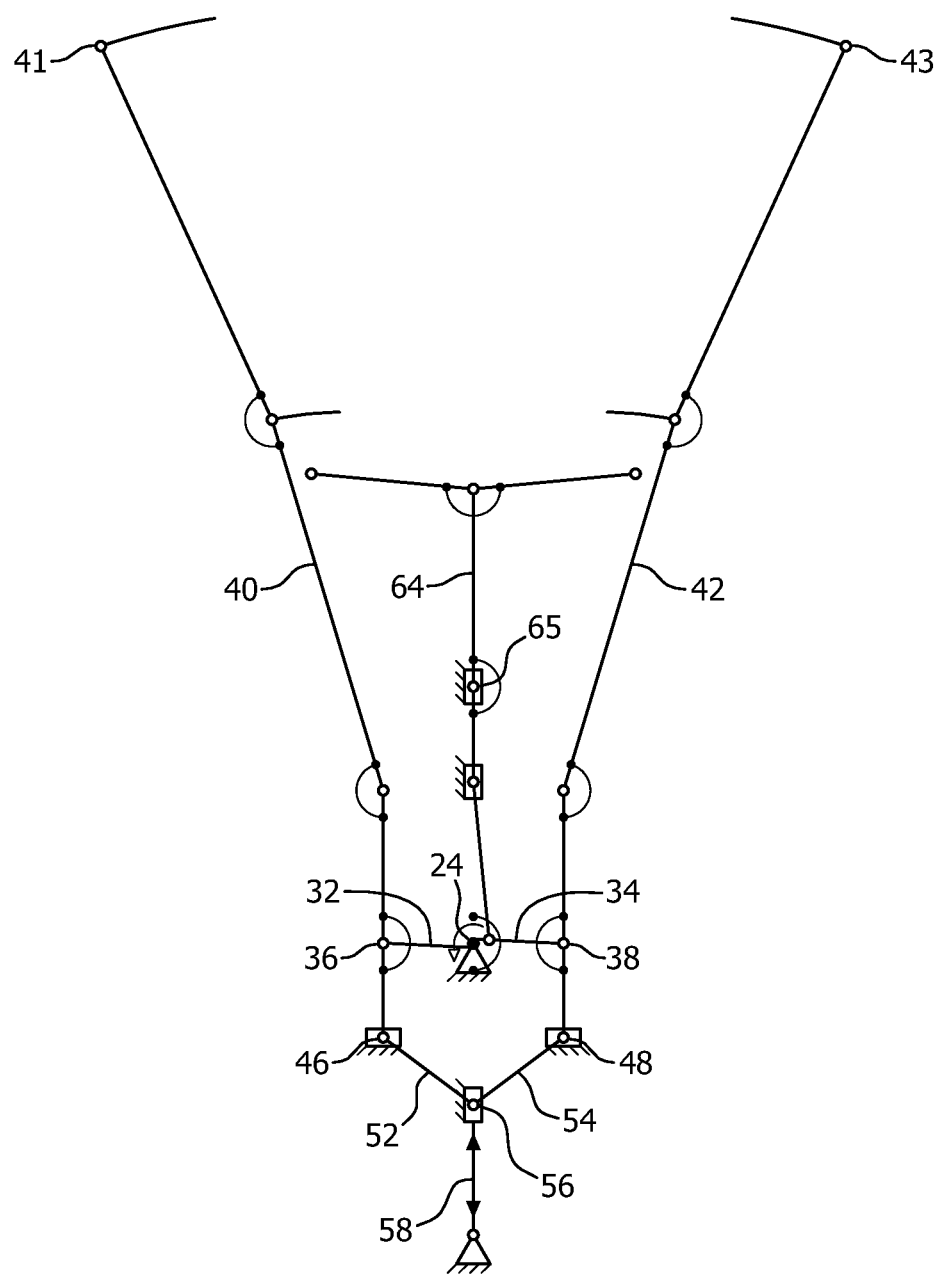
FIG. 3 is a simplified diagram of the drive train arrangement for the mouthpiece assembly of FIGS. 1 and 2.

The above arrangement of FIG. 1-3 produces a reliable in and out action of the side portions, with resulting effective cleansing of the side regions teeth as the bristles make contact with the teeth.

In the embodiment of FIGS. 1-3, the center portion 18 of the mouthpiece receiving assembly is driven directly by a center connecting arm 64. Connecting arm 64 rides in bearings 65 to produce a smooth movement. In the embodiment shown, the length of the stroke of center portion is approximately 0.5 mm, but can vary, such as within a range of 0.25 mm-1.0 mm or even more, in some cases, even to 10 mm.

Figure 4:
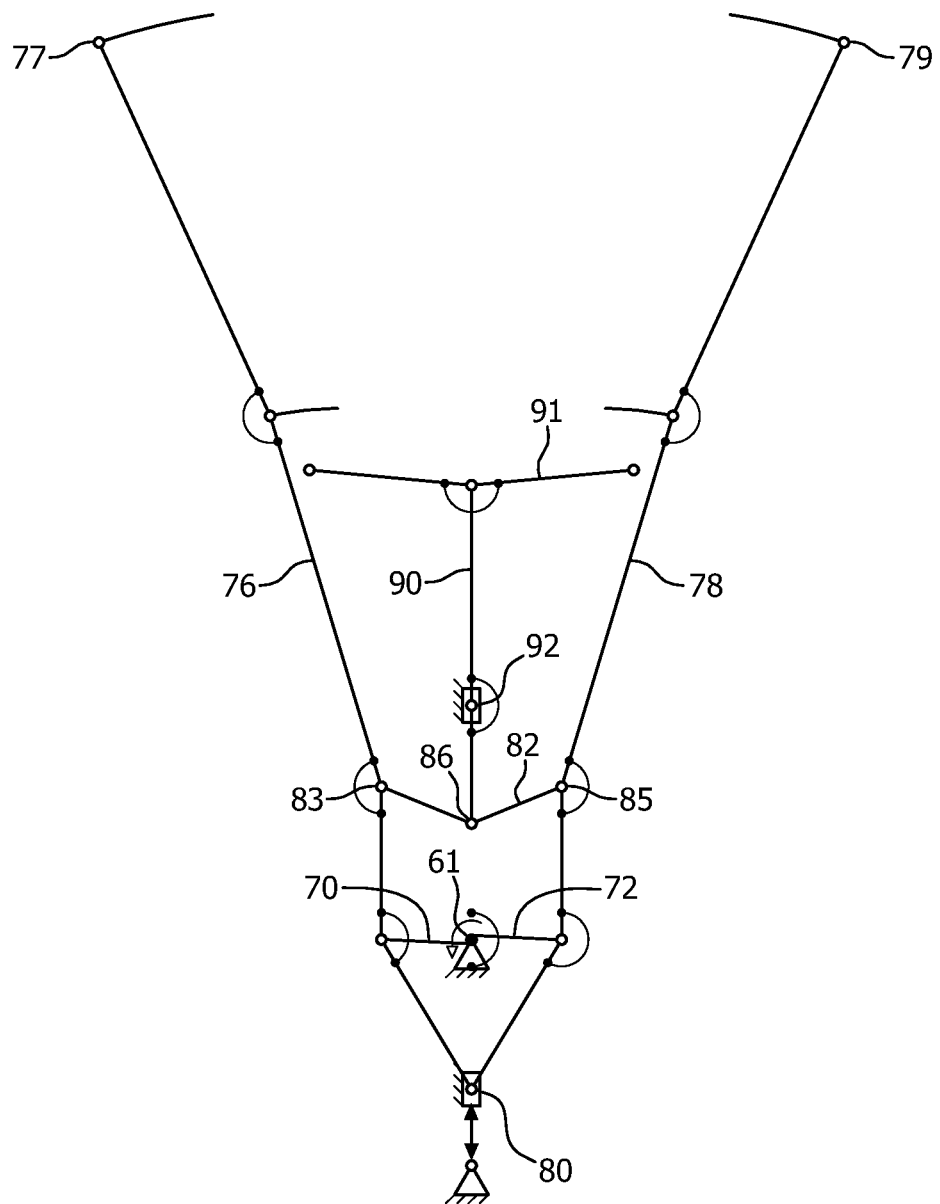
FIG. 4 is a simplified diagram of an alternative drive train arrangement.

An alternative to the arrangement of FIGS. 1-3 is shown diagrammatically in FIG. 4. In this arrangement, a motor and eccentric assembly 61 drives two opposing side drive arms 70 and 72 outwardly and inwardly, as with the embodiment of FIGS. 1-3. This action drives opposing connecting arms 76 and 78 outwardly and inwardly about a single fixed rear pivot point 80. The free ends 77, 79 of connecting arms 76 and 78 are connected to side sections of the teeth receiving assembly (not shown), so that the side sections move against and away from the teeth, providing a cleaning action.

Connecting arms 76 and 78 are connected by a center arm 82 at spaced pivot points 83, 85. Center drive arm 82 itself has a pivoting center point 86. Connected to center drive arm 82 is an intermediate arm 90 which is connected to a center section 91 of the teeth receiving assembly. The intermediate arm 90 moves toward and away from the teeth through a bearing 92. Both of the embodiments of FIGS. 1, 2 and 3 and FIG. 4, respectively, produce the desired in and out movement of three separate teeth receiving sections, making bristle contact with the teeth to produce cleaning of the teeth. The embodiment of FIG. 4 produces movement of the center section by virtue of movement of the side section connecting arms instead of directly from the motor and eccentric assembly.

Figure 5:
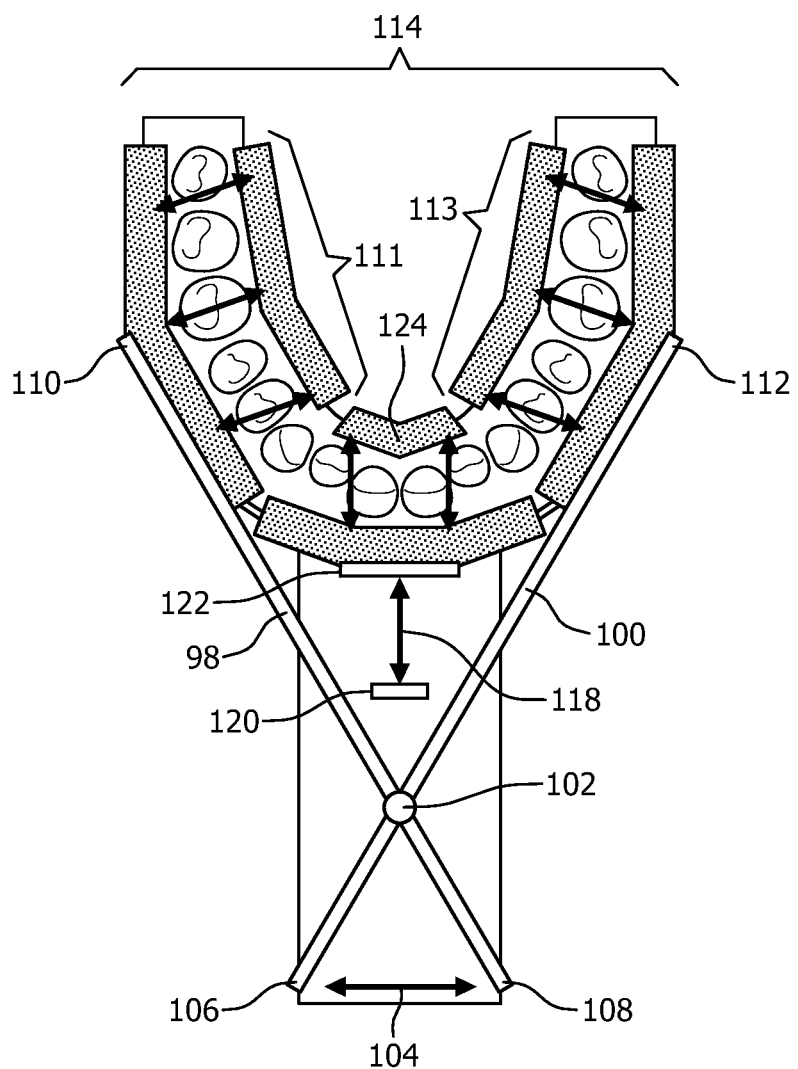
FIG. 5 is a simplified diagram of another drive train arrangement.

FIG. 5 shows another embodiment in simplified schematic form. It includes two elongated connecting arms 98 and 100 linked by a center pivot point 102. Linear motor 104 extends between lower ends 106, 108 of the connecting arms 98 and 100. In operation, linear motor 104 will move ends 106 and 108 directly toward and away from each other, which will result in opposing ends 110 and 112 of arms 98, 100 which are connected to the side portions 111, 113 of a teeth receiving assembly 114 and moving toward and away from the teeth, with the bristles on the side portions making contact with the teeth to produce a cleansing action for the side regions of the teeth. A second linear motor 118 is positioned between a fixed member 120 and a moveable member 122 which is attached to a center section 124 of the teeth receiving assembly. The motor 118, and members 120 and 122 are positioned between pivot point 102 and the teeth. The linear motor 118 will move the center section 124 towards and away from the teeth producing a cleansing action on the center portion of the teeth when the bristles on the center section make physical contact with the teeth.

Figure 6:
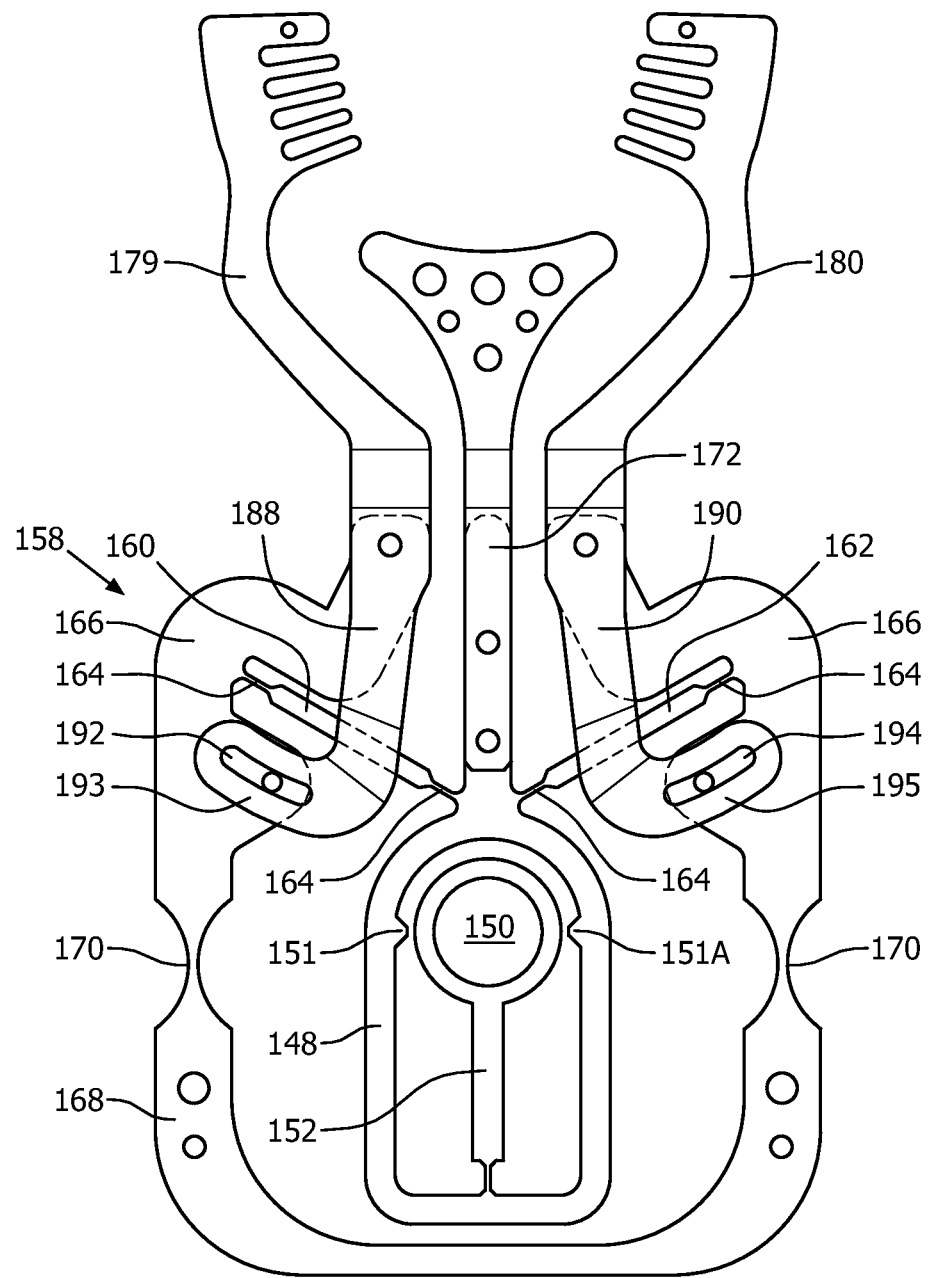
FIGS. 6-8 are partial top and perspective views of another embodiment.
Figure 7:
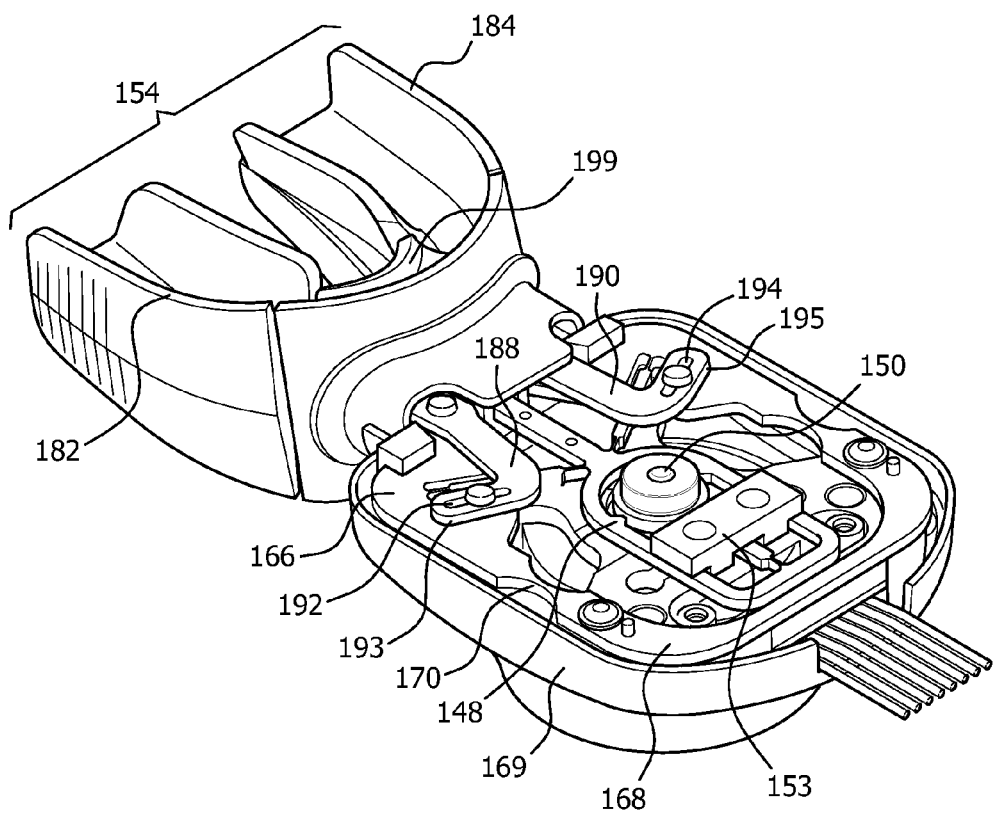
Figure 8:
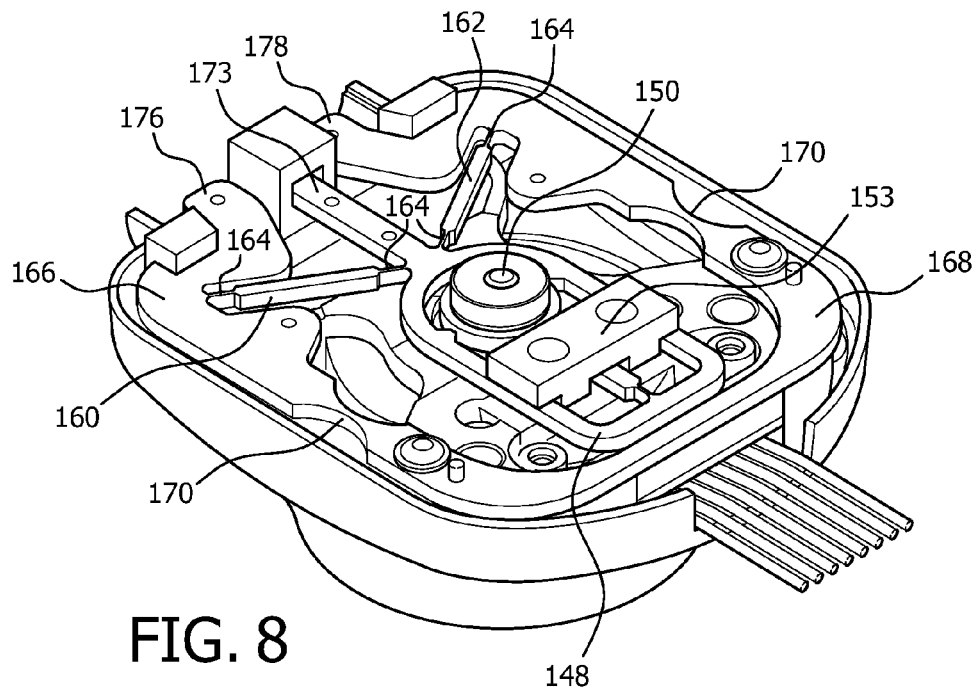

Another embodiment is shown in FIGS. 6-8. This embodiment also includes a DC motor assembly 150, which includes a motor and an eccentric mass like that for the above embodiments. The motor assembly 150 is connected to an inner frame member 148 by opposing connecting hinge members 151, 151A and by a connecting arm and hinge member 152. The inner frame member 148 is shaped in such a way, with hinge members 151, 151A that horizontal (side-to-side) movement of the inner frame is limited, yet movement in the vertical direction is free, toward and away from the teeth receiving assembly. The inner frame member 148 is supported by a bearing 153 which is fixed to the appliance so that the inner frame member with the connecting hinge members are free to move relative to the motor. The inner frame member 148 is secured to an outer frame member 158 by two elongated connecting arms 160 and 162 (FIG. 8). The connecting arms 160 and 162 are connected to the inner and outer frame members by hinge elements 164 located at the opposing ends thereof. In the embodiment shown, the connecting arms 160, 162 extend at an angle of approximately 45° from the horizontal between the inner and outer frame members. Both the inner and outer frame members in the embodiment shown are made from steel, although they could be made from other materials, such as plastic, as well. Typically, the hinge members, however, will be made from steel.

The outer frame member comprises upper and lower portions 166 and 168 with hinge elements 170 connecting the two portions. Lower section 168 is fixed to the frame 169 of the appliance so that it does not move in operation, while the upper portion 166 is free to move outwardly about hinge members 170 in response to movement of the inner frame member toward and away from the teeth by action of the motor assembly, specifically rotation of the motor drive shaft and the eccentric mass mounted thereon. Connecting arms 160, 162 extend to the upper portion of the outer frame member, and thereby provide the required motion of the upper portion of the outer frame member.

Extending from the upper end of inner frame member 148 is a center drive assembly 172, which includes a center frame arm 173 (FIG. 8), the distal end of which drive assembly 172 is connected to a center portion 177 of the teeth receiving assembly 174. The upper portion 166 of the outer frame member 158 terminates in two spaced-apart free ends 176 and 178. Pivotally connected to the free ends 176, 178 are side portion drive arms 179 and 180 which drive the opposing side portions of the mouthpiece side portions 182 and 184 of the teeth receiving assembly. In operation, rotation of the DC motor shaft will result in up/down movement of the inner frame member toward and away from the teeth receiving assembly, which results in a movement of the center drive assembly 172 directly toward and away from the teeth and an outward/inward movement of drive arms 179 and 180 about hinge members 170, resulting in movement of side portions 182 and 184 of the teeth receiving assembly toward and away from the teeth, cleaning the teeth by contact between the bristles on the teeth receiving assembly and the teeth.

In the embodiment of FIGS. 6-8, side portion drive arms 179 and 180 extend downwardly with extended portions 188 and 190 from their point of pivoting connection with free ends 176 and 178 of the upper portion of the outer frame member. The extended portions 188 and 190 of arms 179 and 180 extend downwardly and then outwardly (angling upwardly in sections 193, 195) to overlap a part of the upper portion of the outer frame member. Each extended portion 188 and 190 includes a slot 192 near the free ends thereof, in the angled sections 193, 195. Riding in each slot 192 is a pin 194 (FIG. 7) which extends from the upper portion of the outer frame member. This arrangement, while not necessary, allows the two side portion drive arms to be positionable so as to accommodate different sized teeth arrangements, similar to the adjustment member in the embodiment of FIGS. 1-3.

Figure 9:
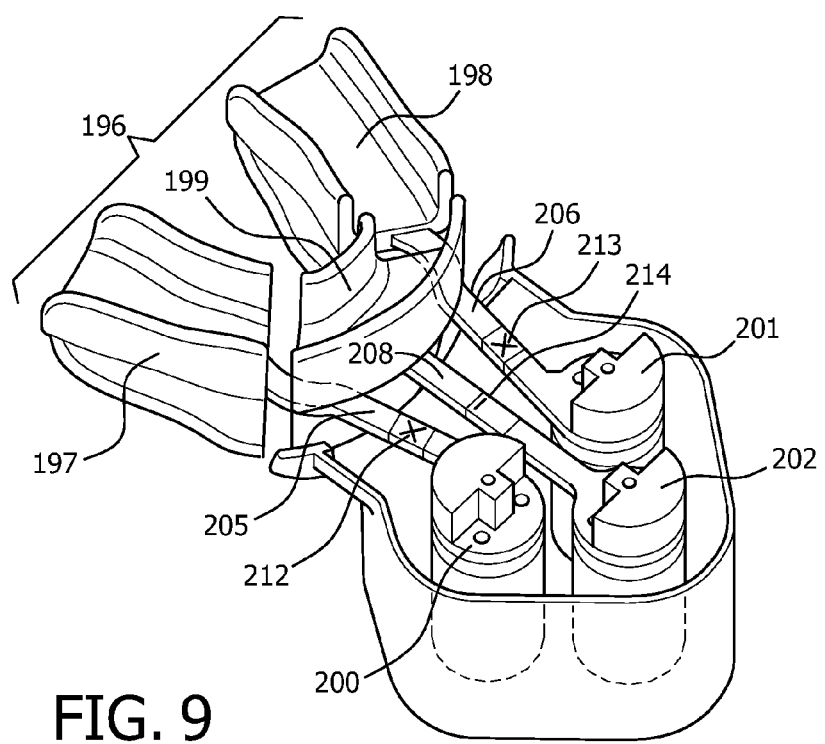
FIG. 9-13 are perspective, cross-sectional and top views of another embodiment.
Figure 10:
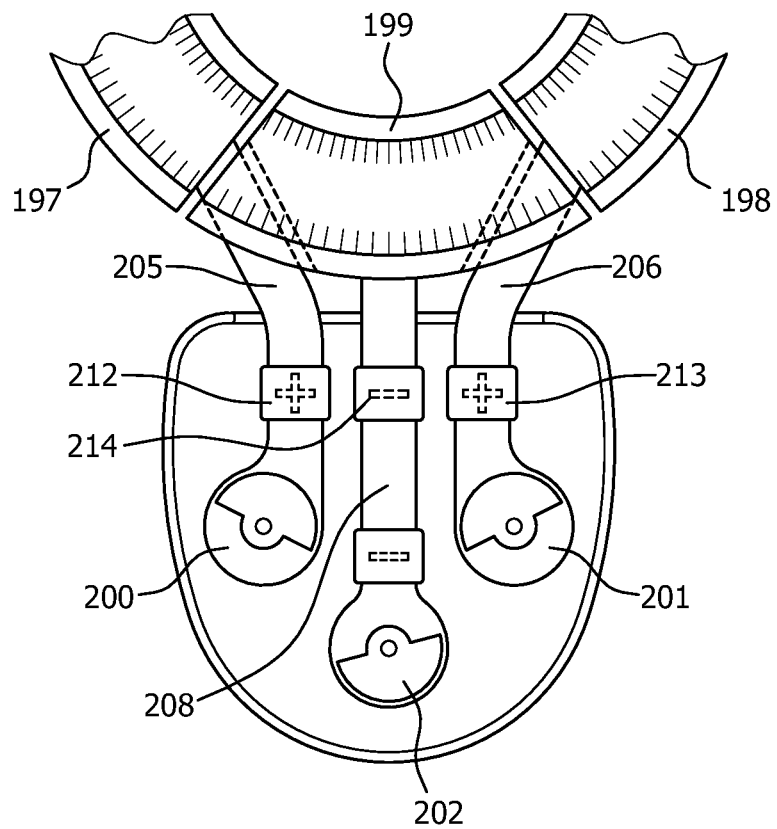

FIGS. 9-13 show another embodiment for a teeth cleaning mouthpiece with a mechanical drive train. FIG. 9 shows a mouthpiece with a teeth receiving assembly 196 which has two opposing side portions 197, 198 and an intermediate center portion 199, like the embodiments shown above. Fewer or more individual portions could be used, however. The two side portions and the center portion are driven separately by DC motors 200-201 for the side portions and 202 for the center portion. Each DC motor has an eccentric mass mounted on an output shaft thereof. The desired frequency range of the motor is 20-270 Hz, preferably approximately 100 Hz. In the embodiment shown, the offset radius of the eccentric will be between 0.2 and 10 mm, preferably approximately 2 mm, while the mass of the eccentric will be between 0.03 and 20 grams, preferably approximately 5 grams.

Extending from the motor assemblies are three drive arms, with drive arms 205 and 206 being associated with the side portions of the teeth receiving assembly and drive arm 208 being associated with center portion 199.

The embodiment of FIGS. 9-13 includes supporting spring assemblies 212-214 which extend downwardly from each drive arm to a frame/housing portion of the mouthpiece appliance. The springs 212-214 are all made from spring steel but have different configurations to provide the required motion for each separate portion of the teeth receiving assembly of the mouthpiece. The springs could also be made from other materials, such as plastic.

Figure 11:
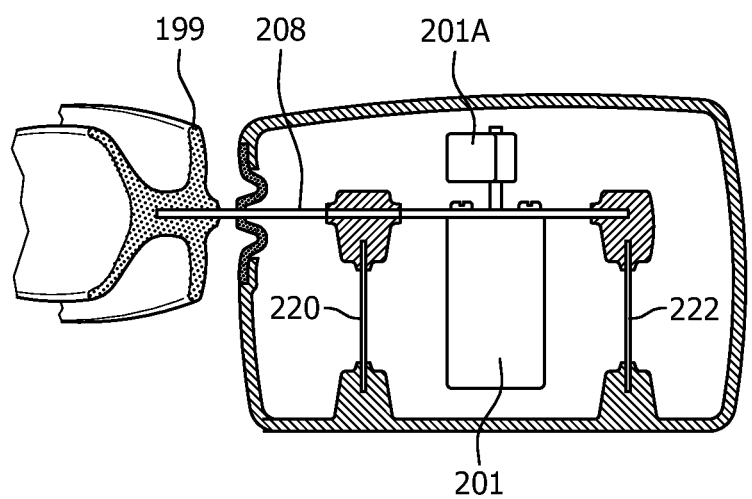
Figure 12:
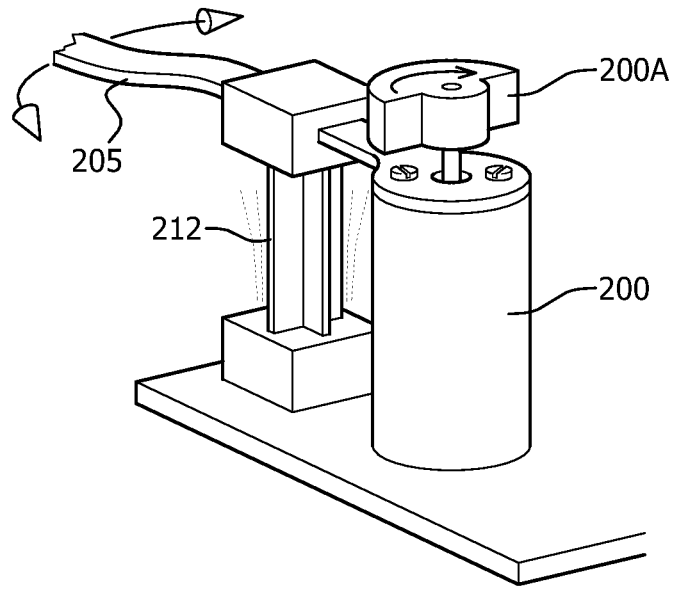
Figure 13:
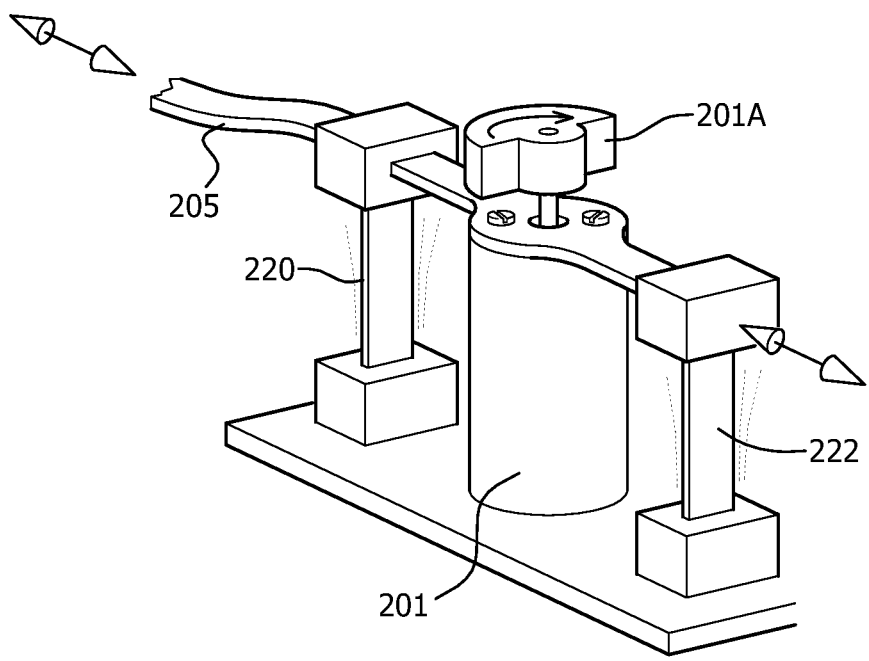

The springs for the two side portions have an X shape in cross-section, shown in detail in FIG. 12. FIG. 12 also shows motor 200 and its eccentric mass 200A. In the embodiment shown, the springs 212 and 214 are approximately 20 mm long, 5 mm wide and 0.2 mm thick. The X configuration is designed so as to be weak in the rotational dimension, thereby permitting movement in the rotational direction which in turn permits the ends of the drive arms 205, 206 and the side sections to which they are connected to move in and out, toward and away from the teeth, resulting in cleansing of the side teeth with bristle contact with the teeth. The spring assembly for center drive arm 208, shown in FIGS. 11 and 13, includes two spaced metal leaf springs 220, 222. FIGS. 11 and 13 also show motor 201 and its eccentric mass 201A. The two leaf springs are separated by approximately 15 mm, and are approximately 20 mm long, and 5 mm wide and 0.2 mm thick. The leaf springs are oriented laterally across the drive arm 208, so as to permit motion of the drive arm toward and away from the teeth, due to the relative thinness of the leaf springs, but prevents motion laterally, due to the width of the spring and rotationally, due to the use of two springs and the spacing between them.

The configuration of the springs is important, since it allows movement of the drive arm in a desired direction while tending to prevent movement in other directions.

The advantage of the drive train shown in FIGS. 9-13 is that it is force driven, meaning that the maximum force produced against the teeth cannot exceed a certain value, determined by the mass of the eccentric, the eccentric offset and the RPM of the motor. As is clear from the above, the drive train of FIGS. 9-13 is actually three independent drive trains, so that the separate sections of the mouthpiece can be moved completely independently.

Figure 14:
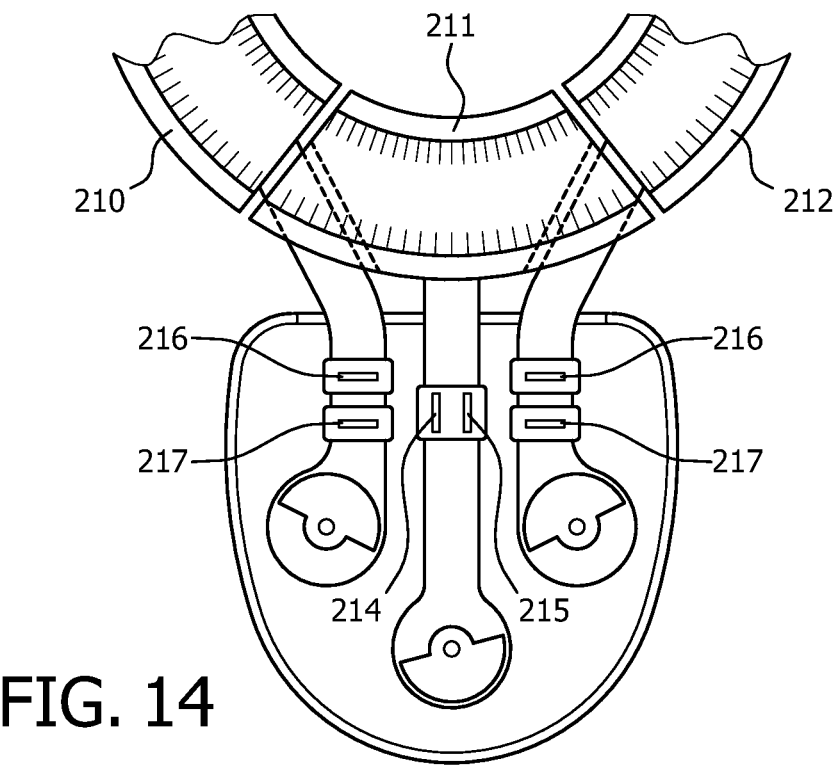
FIG. 14 is a top view of a variation of the embodiment of FIGS. 9-13.

While the spring arrangement shown in FIGS. 9-13 produces an in and out movement of the teeth receiving sections, generally toward and away from the teeth, other spring arrangements can be produce different brushing actions. One such arrangement is shown in FIG. 14. This arrangement produces an action of each individual section 210-212 along or across the surfaces of the teeth. In this arrangement, two leaf springs are provided for the center section. The leaf springs 214, 215, however, are oriented at 90° to that of the embodiment of FIGS. 9-13, i.e., the two leaf springs are positioned parallel with the drive arm for the center sections. The leaf springs have the same length and the same thickness, and are separated by the width of the connecting arms, i.e. 10 mm. The action of the associated DC motor and the eccentric produces a sweeping motion of the center section of the teeth receiving assembly, back and forth across the surfaces of the teeth, as opposed to in and out, towards and away from the teeth, because the arrangement of the springs 214, 215 tends to prevent in and out motion of the connecting arm and the center portion of the teeth receiving assembly.

The leaf spring assemblies for driving the side sections each comprise two spaced leaf springs 216, 217. These leaf springs will be oriented laterally relative to the length of the connecting arms. In the embodiment shown, they will be spaced by approximately 2.5 mm. With respect to these two assemblies, as the DC motor with the eccentric mass turns, the drive arms and the side sections will move back and forth parallel with the surfaces of the teeth. The action of the embodiment of FIG. 14 produces a scrubbing cleaning action with the bristles, instead of a tapping cleaning action, as for FIG. 9-13.

Other motions of the teeth receiving sections can be accomplished using different spring arrangements.

Figure 15:
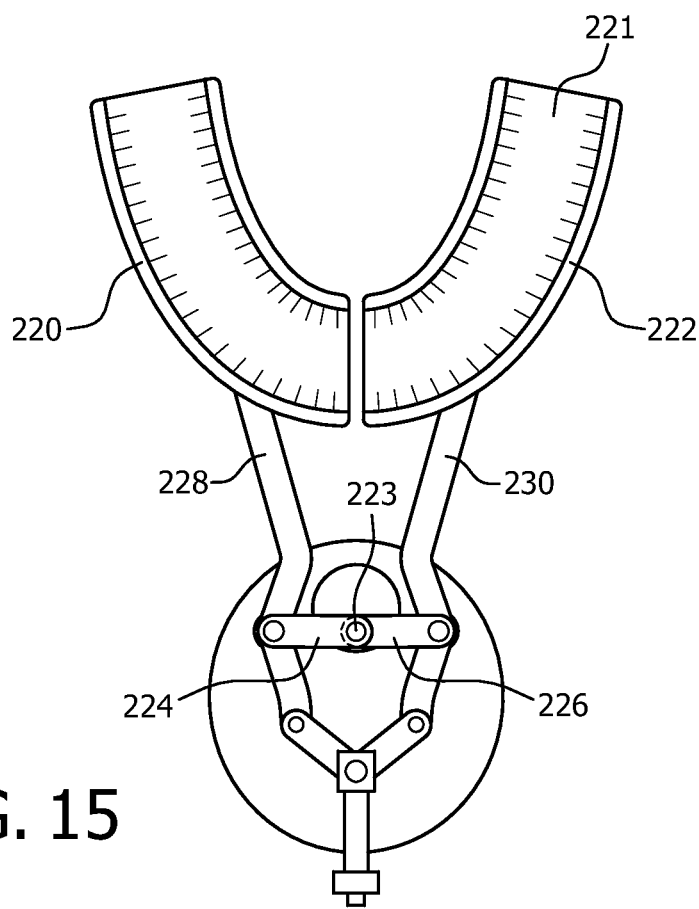
FIG. 15 is a top view of a variation of the embodiment of FIGS. 1-3.
Figure 16:
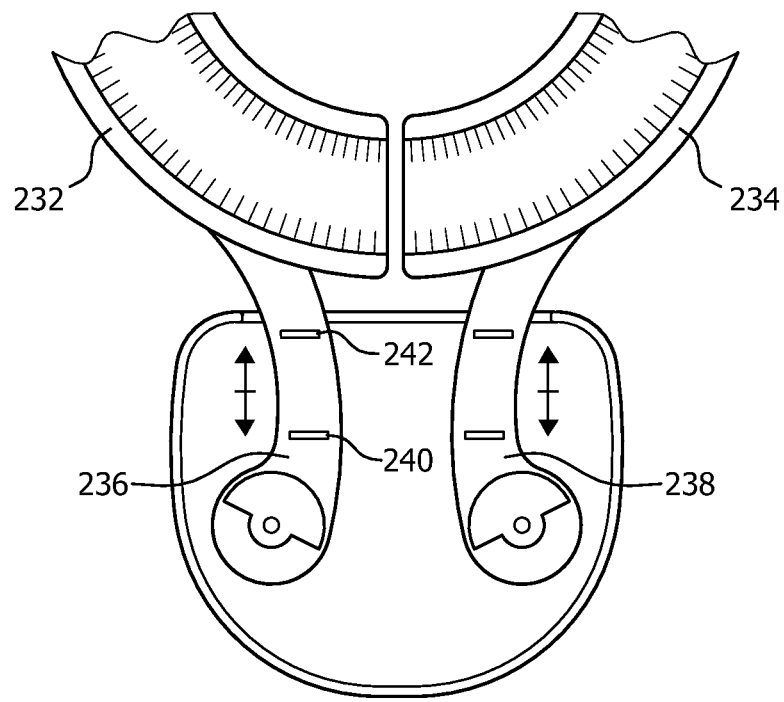
FIGS. 16 and 17 are top views of variations of the embodiment of FIG. 9-13.
Figure 17:
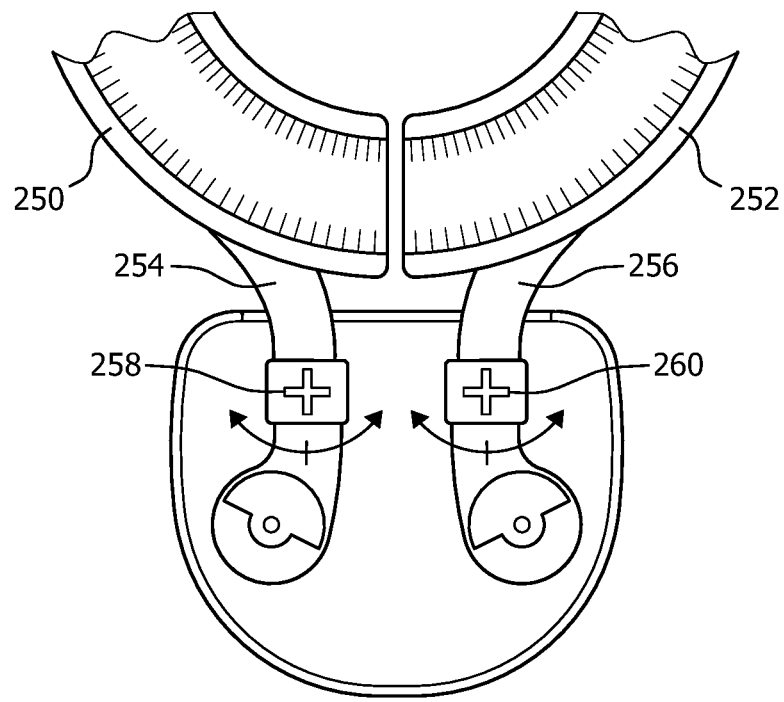

FIGS. 15 and 16-17 illustrate mouthpiece appliances with teeth receiving assemblies comprising just two sections. In FIG. 15, a teeth receiving assembly comprises two sections 220 and 222. A DC motor/eccentric mass assembly 223 drives two opposing drive arms 224 and 226, which in turn drive two connecting arms 228, 230. The connecting arms are connected to sections 220 and 222. This arrangement produces back and forth movement of the drive arms, toward and away from the teeth.

FIG. 16 is comparable to the embodiment of FIGS. 9-13, with two cleaning sections 232, 234 comprising the teeth receiving assembly. An arrangement of leaf springs permit in and out action of the associated drive arms. For each drive arm 236, 238, there are two spaced leaf spring, e.g. leaf springs 240 and 242 for drive arm 236. For FIG. 17, with two sections 250, 252 and two drive arms 254, 256, two X configuration spring assemblies 258 and 260 provide a rotating action of the drive arms, about the motor assemblies, with corresponding movement of the two cleaning sections.

While the embodiments described above include a DC motor, an AC motor can also be used. Further, while bristles have been disclosed for cleaning, other cleaning elements, such as foam elements, could be used effectively as well.

Accordingly, a mouthpiece appliance to clean teeth has been disclosed which includes a teeth receiving mouthpiece, comprising three sections or in some cases two sections, for cleaning of the teeth. More than two sections is also possible A mechanical drive train using a DC motor and an eccentric mass is used to drive separate connecting arms which are connected to the mouthpiece sections. In one embodiment a single motor assembly is used with an arrangement of connecting arms to produce desired in and out motion of the brushhead sections toward and away from the teeth. In another arrangement, a separate motor is used for each mouthpiece section, with a spring support arrangement for each drive arm to provide the cleansing action for the teeth, including both in and out action or action across the teeth. With this embodiment, other cleansing motions can be achieved.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A mouthpiece for cleaning teeth, comprising:
   an assembly for receiving teeth which includes two side portions and an intermediate center portion, wherein the side portions and the center portion include bristle sections which are adapted to clean teeth upon contact between the bristle sections and the teeth of the user;
   three motor assemblies, each with an eccentric weight mounted on an output shaft thereof;
   first, second and third drive arms which extend, respectively, between the respective motor assemblies and the side and center portions of the teeth receiving assembly; and
   first, second and third spring assemblies which connect the drive arms to a body portion of the appliance, wherein each of the spring assemblies, respectively, is configured to permit movement of their associated drive arm in one direction which results in cleansing of the teeth, but substantially prevents movement of the same drive arm in other directions.

2. The mouthpiece of claim 1, where the motor assemblies each include a DC motor.

3. The mouthpiece of claim 2, wherein the DC motor assemblies are unsupported within the appliance, respectively, other than by their associated drive arm and spring assembly.

4. The mouthpiece of claim 2, wherein the DC motors run at a frequency in the range of 20-270 Hz and the eccentric has a mass of between 0.3 and 20 grams and an offset radius between 0.2 and 10 mm.

5. The mouthpiece of claim 2, wherein the spring assemblies for the two side portions are springs having an X shape in cross-section, permitting rotational motion of the associated drive arms, but preventing motion in other dimensions, and wherein the spring assemblies for the center portion comprises two spaced leaf springs oriented laterally relative to the drive arm to the center portion, permitting movement of the associated drive arm toward and away from the teeth, but substantially preventing movement in other dimensions.

6. The mouthpiece of claim 2, wherein the spring assemblies for the two side portions each include two spaced leaf springs oriented laterally across the drive arms, permitting motion of the side portions along the teeth and tending to prevent motion in other dimensions, and wherein the spring assembly for the center portion drive arm comprise two parallel leaf springs oriented parallel with the drive arm, permitting motion of the center portion along the front surfaces of the teeth and tending to prevent movement of the center portion in other dimensions.

* * * * *